United States Patent [19]

Higgins

[11] Patent Number: Plant 6,406

[45] Date of Patent: Nov. 22, 1988

[54] APPLE TREE — HIGRED CULTIVAR

[75] Inventor: George Higgins, Grandview, Wash.

[73] Assignee: Stark Brothers Nurseries and Orchards Company, Louisiana, Mo.

[21] Appl. No.: 923,429

[22] Filed: Oct. 27, 1986

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—Burns, Doane, Swecker & Mathis

[57] ABSTRACT

A new and distinct variety of Jonathan apple tree is provided which originated as a limb mutation of the Snyder cultivar of U.S. Plant Pat. No. 2,650. The new variety produces attractive red variable-sized fruit which colors approximately 10 to 14 days earlier than the fruit of the Snyder cultivar. Also, the fruit of the new variety exhibits a brighter red appearance and is formed more abundantly and more consistently than the fruit of the Super Jon cultivar of U.S. Plant Pat. No. 5,086.

1 Drawing Sheet

SUMMARY OF THE INVENTION

The new and distinct variety of Jonathan apple tree was discovered by me in 1972 while present as a limb mutation in my orchard at Grandview, Wash. Such mutation originated on a tree of the Snyder cultivar of U.S. Plant Pat. No. 2,650. The parent Snyder cultivar was marketed under the NURED trademark by the C & O Nursery of Wenatchee, Wash.

At the time of the discovery I noticed that fruit borne on the limb of a single tree had colored to a complete or solid red striped appearance while fruit on other nearby trees of the Snyder cultivar exhibited only faint red stripes. Such tree was marked so that its distinctive characteristics could be confirmed during subsequent growing seasons.

The new variety was found to consistently bear large crops of attractive variable-sized fruits which possess a bright red overall appearance. The bright red coloration is faintly striped over a light red ground color. Such light red ground color accordingly tends to enhance the overall red appearance of the fruit.

Asexual propagation was performed on my behalf by personnel of Stark Brothers Nurseries and Orchards Company at Louisiana, Mo. during the summer of 1977. This and subsequent propagations has established that the unique combination of characteristics of the new variety comes true to form and is established and is transmitted through succeeding generations.

It has been confirmed that the new Jonathan apple variety exhibits:

(a) the formation of variable-sized red fruits which color approximately 10 to 14 days earlier than those of the Snyder cultivar of U.S. Plant Pat. No. 2,650,
(b) the formation of fruit having a brighter red appearance than that of the Super Jon cultivar of U.S. Plant Pat. No. 5,086, and
(c) the formation of fruit on a more abundant and a more consistent basis than the Super Jon cultivar of U.S. Plant Pat. No. 5,086.

The new variety of Jonathan apple tree has been named the Higred cultivar and is being marketed by Stark Brothers Nurseries and Orchards Company under the Ultrared trademark.

BRIEF DESCRIPTION OF THE PHOTOGRAPH

The accompanying photograph shows typical specimens of the fruit and foliage of the new variety in color as nearly true as it is reasonably possible to make the same in a color illustration of this character.

DETAILED DESCRIPTION OF THE NEW VARIETY

The following is a detailed description of the new variety where color terminology is to be accorded its ordinary dictionary significance except where otherwise indicated. The specimen described was grown at Louisiana, Pike County, Mo.

Representative dates of first and last pickings were Aug. 21, 1985 and Aug. 30, 1985 respectively.

Tree: Medium large; medium vigorous, upright and spreading; round-topped; medium rapid growing; hardy; very productive; regular bearing.

*Trunk.*—Medium stocky; shaggy.

*Branches.*—Medium thick; medium smooth; medium branching; grey in coloration. Lenticels — few in number; small.

*Leaves.*—Medium large; medium wide; medium long; ovate; taper-pointed; medium thick; rugose. Upper surface — dark yellowish-green, Plate XVIII, Color No. 33′ GY-G, tone m of Ridgeway Color Standards and Nomenclature. Under surface — Lettuce Green, Plate V, Color No. 29, tone k of Ridgeway Color Standards and Nomenclature. Length — approximately $2\frac{3}{4}$ inches. Width — approximately 1 9/16 inches. Margin — coarsely serrate. Petiole — medium long (approximately 13/16 inch); medium thick.

Flowers: Medium early; medium large; pink. Representative dates of first and full bloom were Apr. 16, 1985 and Apr. 23, 1985, respectively.

Fruit:

*Maturity when described.*—Hard ripe — Aug. 21, 1985.

*Size.*—Variable. Axial diameter — approximately $2\frac{3}{8}$ to $2\frac{3}{4}$ inches. Transverse diameter — approximately $2\frac{3}{4}$ to $2\frac{7}{8}$ inches.

*Form.*—Uniform; compressed laterally; truncate at base.

*Cavity.*—Symmetrical; acuminate; slightly furrowed. Depth — approximately ½ to ¾ inch. Breadth — approximately ⅞ inch. Markings — some russet.

*Basin.*—Unsymmetrical; abrupt at base; wide base. Depth — approximately 7/16 inch. Breadth — approximately ¾ to ⅞ inch.

*Calyx.*—Closed; segments persistent; broadly lanceolate; imbricate at base. Length — approximately ⅛ inch. Outer-surface — pubescent. Inner-surface — pubescent.

*Eye.*—Closed.

*Skin.*—Thin; tough; smooth; glossy; waxed. Dots — obscure; small; even; circular. Color of dots — vinaceous Buff, Plate XL, Color No. 17, tone d of Ridgeway Color Standards and Nomenclature. Distribution of dots — widely scattered. Ground color — Napal Red, Plate I, Color No. 3, tone i of Ridgeway Color Standards and Nomenclature. Color of Markings — faintly striped; bright. Oxblood Red, Plate I, Color No. 1, tone k of Ridgeway Color Standards and Nomenclature. Bloom — abundant. Scarfskin — wanting. General Color Effect — bright red with faint dark red stripes.

*Flesh.*—Juicy. Color — dull white with yellowish tint. Texture — firm; crisp. Flavor — sub-acid; sprightly; enhanced with rich sweet aftertaste. Aroma — pronounced. Quality — good. Core — median. Bundle area — medium small; oblate symmetrical at base. Bundle color — green; conspicuous, in two whorls. Alternate bundle — approximate to calyx; reaches tube below stamens. Core lines — clasping; in cross-section distinct. Carpellary area — distinct; small. Calyx tube — pubescent; cone shaped. Depth of calyx tube to shoulder — approximately ⅜ inch. Entire depth — approximately 11/16 inch. Styles — present. Stamens — in two distinct whorls; basal. Auxillary cavity — wanting. Seed cells — axile; closed. Surface — fissured-smooth. Cross-section — broad.

*Seeds.*—Number perfect — 4; number imperfect — 3. Number in one cell — 2. Length — approximately ⅜ inch. Breadth — approximately 3/16 inch. Form — acuminate.

Use: Market; dessert.

Keeping quality: Good.

Resistance to:

*Insects.*—Medium.

*Diseases.*—Medium.

I claim:

1. A new and distinct variety of Jonathan Apple tree, substantially as illustrated and described, characterized by (a) the formation of variable-sized red fruits which color approximately 10 to 14 days earlier than those of the Snyder cultivar of U.S. Plant Pat. No. 2,650, (b) the formation of fruit having a brighter red appearance than that of the Super Jon cultivar of U.S. Plant Pat. No. 5,086, and (c) the formation of fruit on a more abundant and a more consistent basis than the Super Jon cultivar of U.S. Plant Pat. No. 5,086.

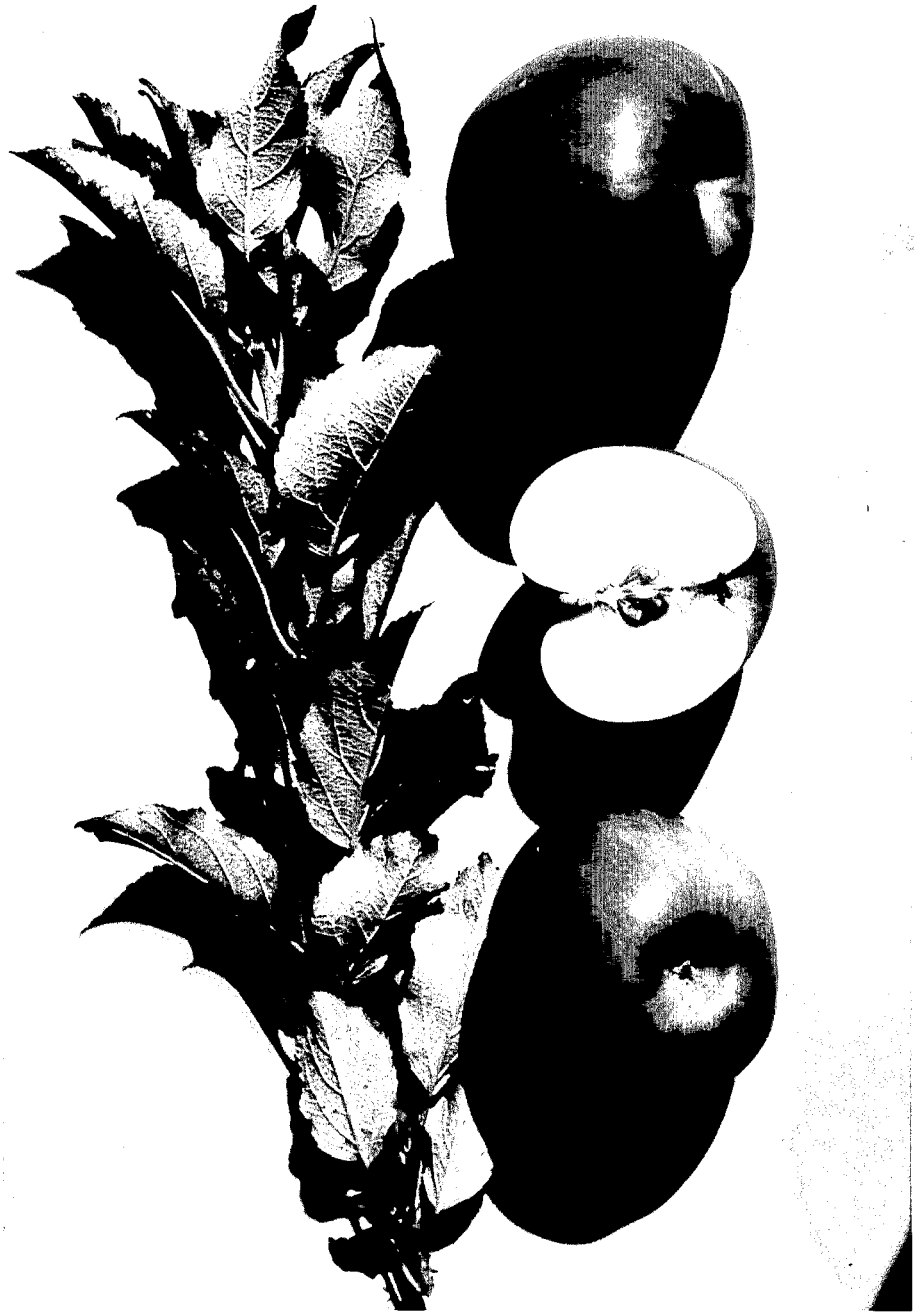

* * * * *